US012577196B2

(12) United States Patent
Babikian et al.

(10) Patent No.: US 12,577,196 B2
(45) Date of Patent: Mar. 17, 2026

(54) QUATERNARY AMINE COMPOUNDS WITH ISOPROPYLMETHYLPHENOL ESTER MOIETIES AS ANTIVIRALS, ANTIBACTERIALS AND ANTIMYCOTICS

(71) Applicant: Rhea Genetics PTE. LTD., Singapore (SG)

(72) Inventors: Haig Babikian, Singapore (SG); Benjamin Jiaravanon, Singapore (SG)

(73) Assignee: Rhea Genetics PTE. LTD., Singapore (SG)

( * ) Notice: Subject to any disclaimer, the term of this patent is extended or adjusted under 35 U.S.C. 154(b) by 1186 days.

(21) Appl. No.: 17/603,780

(22) PCT Filed: Apr. 16, 2020

(86) PCT No.: PCT/IB2020/053607
§ 371 (c)(1),
(2) Date: Oct. 14, 2021

(87) PCT Pub. No.: WO2020/212901
PCT Pub. Date: Oct. 22, 2020

(65) Prior Publication Data

US 2022/0213024 A1 Jul. 7, 2022

(30) Foreign Application Priority Data

Apr. 16, 2019 (GB) ..................................... 1905390

(51) Int. Cl.

| | |
|---|---|
| ***C07C 229/38*** | (2006.01) |
| ***A61P 31/04*** | (2006.01) |
| ***A61P 31/10*** | (2006.01) |
| ***A61P 31/22*** | (2006.01) |
| ***C07C 227/16*** | (2006.01) |

(52) U.S. Cl.
CPC ............ *C07C 229/38* (2013.01); *A61P 31/04* (2018.01); *A61P 31/10* (2018.01); *A61P 31/22* (2018.01); *C07C 227/16* (2013.01)

(58) Field of Classification Search
None
See application file for complete search history.

(56) References Cited

U.S. PATENT DOCUMENTS 10,858,308 B2 * 12/2020 Babikyan .............. C07C 229/16

FOREIGN PATENT DOCUMENTS

| | | | |
|---|---|---|---|
| CN | 1683317 | A | 10/2005 |
| CN | 105503631 | A | 4/2016 |
| EP | 3153156 | A1 | 4/2017 |
| GB | 1258924 | A | 12/1971 |
| JP | S50125724 | A | 10/1975 |
| JP | H03246263 | A | 11/1991 |
| JP | 2005162769 | A | 6/2005 |
| WO | 9709988 | A1 | 3/1997 |
| WO | 2000057730 | A1 | 10/2000 |
| WO | 2004020729 | A1 | 3/2004 |

(Continued)

OTHER PUBLICATIONS

Lisetski (Mol. BioSyst., 2014, 10, 3155-3162) (Year: 2014).*

(Continued)

*Primary Examiner* — John S Kenyon
*Assistant Examiner* — Rehana Ismail
(74) *Attorney, Agent, or Firm* — Wood Herron & Evans LLP

(57) ABSTRACT

Disclosed are compounds having the following formula (I):Formula (I) wherein R is an alkylene chain having between 8 and 20 carbon atoms, and A is one or more anions having a total charge of −2, or R is a quaternary amine having the following formula (Ia):Formula (Ia) wherein $R_a$ and $R_b$ are each an alkylene chain having between 8 and 20 carbon atoms, and A is one or more anions having a total charge of −3; $R_1$, $R_2$, $R_3$, $R_4$, $R_5$ and $R_6$ are each independently selected from $C_{1-10}$ alkyl and H; E has the following Formula (Ib), wherein the ester oxygen is bonded to the aromatic ring of each E at the same position, the position being position 2 or 3; and wherein $R_E$ is H or a halide.

(I)

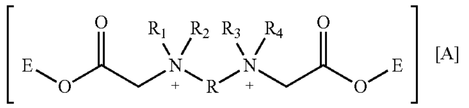

(Ia)

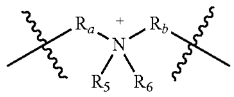

(Ib)

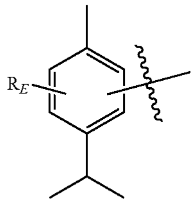

19 Claims, No Drawings

(56) References Cited

FOREIGN PATENT DOCUMENTS

| | | | |
|---|---|---|---|
| WO | 2015067603 | A1 | 5/2015 |
| WO | 2016007821 | A2 | 1/2016 |
| WO | 2017003403 | A1 | 1/2017 |
| WO | 2018132066 | A1 | 7/2018 |

OTHER PUBLICATIONS

International Search Report and Written Opinoin in International Patent Application No. PCT/IB2020/053607, dated Oct. 8, 2020, 7 pgs.
Chinese Office Action in Chinese Patent Application No. 2020800393663, dated Nov. 2, 2023, 6 pgs.
Sharma, M. L. et al., “Synthesis and Plant Growth Retardant Activity of Quaternary Ammonium Salts Containing Phenyl In-Butyl Ethanoate Moieties,” Pesticide Research Journal, 2008, vol. 20(2), p. 178-182.
Carbone-Howell et al. (2014), caplus an 2014:560756.
Chayavichitsilp P, Buckwalter JV, Krakowski AC, Friedlander SF (Apr. 2009). “Herpes Simplex”. Pediatr Rev. 30 (4).
Combined Search and Examination Report in Application No. GB1700404.5, dated Oct. 31, 2017, 6 pgs.
Combined Search and Examination Report in Application No. GB1905390.9, dated Aug. 7, 2019, 6 pgs.
International Search Report and Written Opinion in International Patent Application No. PCT/SG2018/050012, mailed Mar. 19, 2018, 9 pgs.
Ljubojevic, Suzana; Skerlev, Mihael (2014). “HPV-associated diseases”. Clinics in Dermatology. 32 (2): 227-234.
Milner, Danny A. (2015). Diagnostic Pathology: Infectious Diseases. Elsevier Health Sciences. p. 40.
Office Action in U.S. Appl. No. 16/476,977, dated Jun. 9, 2020, 6 pgs.
Japanese Office Action in Japanese Patent Application No. 2021-562064, dated Mar. 12, 2024, 6 pgs. (English translation included).

* cited by examiner

QUATERNARY AMINE COMPOUNDS WITH ISOPROPYLMETHYLPHENOL ESTER MOIETIES AS ANTIVIRALS, ANTIBACTERIALS AND ANTIMYCOTICS

The present invention relates to compounds that may be used to treat viral infections, bacterial infections and fungal infections.

BACKGROUND

The Herpesviridae is a large family of DNA viruses that are responsible for a number of diseases in both humans and animals. The most common Herpesviradae that cause diseases amongst humans are Varicella Zoster virus, Epstein-Barr virus, Cytomegalovirus, Herpes Simplex virus 1 and Herpes Simplex virus 2.

Varicella zoster virus is a common virus that causes chickenpox in children and herpes zoster (shingles) in adults.

Epstein-Barr virus is the virus that commonly causes infectious mononucleosis (glandular fever), while also being associated with cancers such as Hodgkin's lymphoma, Burkitt's Lymphoma and gastric cancer.

Cytomegalovirus, is further member of the Herpesviridae viral family. Human cytomegalovirus (HCMV, or CMV or human herpersvirus-5 (HHV-5)) is a virus associated with the salivary glands and is typically unnoticed by healthy individuals, but can be life threatening for immunocompromised, such as patients having HIV, recipients of organ transplants and new born infants.

Herpes Simplex Virus 1 and Herpes Simplex Virus 2 are both viruses responsible for the viral disease Herpes Simplex. Both viruses can cause oral infections and genital infections, although HSV-1 is more commonly associated with oral infections (e.g. oral herpes), while HSV-2 is more commonly associated with genital infections (e.g. genital herpes). The Herpes Simplex viruses cause infections that affect between approximately 60% and 95% of adults world wide (Chayavichitsilp P, Buckwalter J V, Krakowski A C, Friedlander S F (April 2009). "Herpes simplex". Pediatr Rev. 30 (4)).

Oral herpes is typically associated with the face and/or the mouth and may result in small blisters that form Herpes labialis (cold sores). Oral Herpes can also include other symptoms such as sore throat, fever, muscle pains, swollen lymph nodes, head ache and malaise, particularly in the first episode after the patient becomes infected.

Genital herpes is typically associated with the genitals and may result in small lesions in the genital regions, inner thigh, buttocks and/or anus. Other typical symptoms associated with this virus include pain, itching, burning, discharge, fever, headache, muscle pain, swollen lymph nodes and malaise.

Oral Herpes may be treated with antiviral drugs, which can reduce the duration of the symptoms, but not completely kill the responsible virus. After the symptoms of an oral herpes infection resolve, the herpes virus (e.g. HSV-1 or HSV-2) generally remains dormant in the facial nerve branches, and the virus may periodically reactivate to create Herpes labialis in the same area of the mouth or face as the site of the original infection. In some humans, the virus remains asymptomatic, although transmission may be possible even when symptoms are not present.

Genital herpes can also be treated with antiviral drugs, which may reduce the duration of the symptoms. However, as for oral herpes, there is no licensed medication that completely eradicates the responsible virus from the human body.

Human Papilloma virus (HPV) is responsible for Human papillomavirus infection which generally cause no symptoms and resolve spontaneously. However, in some cases infections persist and result in warts or precancerous lesions. The precancerous lesions may increase the risk of a number of cancer types, and these include cancer of the cervix, vagina, penis, anus, mouth and throat (Ljubojevic, Suzana; Skerlev, Mihael (2014). "HPV-associated diseases". Clinics in Dermatology. 32 (2): 227-234.). HPV is the most common sexually transmitted infection globally and most people are infected at some point during their lives (Milner, Danny A. (2015). Diagnostic Pathology: Infectious Diseases. Elsevier Health Sciences. p. 40).

Bacterial and fungal infections are common throughout the world. Various drugs have been developed to treat such infections and these may target specific or broad types of bacterial and fungal species and strains. Antibiotic resistance, and more recently antifungal resistance, is becoming more prevalent and an ever increasing problem worldwide. With this in mind, there is a global need for new drugs that are able to treat bacterial and fungal infections.

Bearing in mind the prevalence of the Herpes virus (particularly Herpes Simplex virus) and Human papilloma virus, as well as the range of diseases associated with these viruses, there is a need for a treatment that targets these viruses and can treat the diseases associated with these viruses.

Compounds have been disclosed which have shown anti-bacterial, antifungal and anti-viral effects, examples of such compounds are disclosed in WO2018132066. There is an ongoing need for compounds that have an anti-bacterial, anti-viral and anti-fungal effect.

In a first aspect of the present invention there is provided a compound having the following formula:

(I)

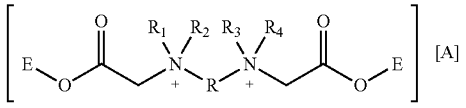

wherein R is an alkylene chain having between 8 and 20 carbon atoms, and A is one or more anions having a total charge of −2;

or R is a quaternary amine having the following formula:

(Ia)

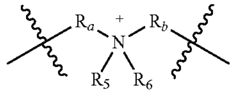

wherein $R_a$ and $R_b$ are each an alkylene chain having between 8 and 20 carbon atoms, and A is one or more anions having a total charge of −3;

$R_1$, $R_2$, $R_3$, $R_4$, $R_5$ and $R_6$ are each independently selected from $C_{1-10}$ alkyl and H; and E has the following formula (Ib)

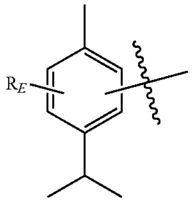

, wherein the ester oxygen is bonded to the aromatic ring of each E at the same position, the position being position 2 or 3; and wherein $R_E$ is H or a halide.

R may be, for example, a linear or branched saturated or unsaturated alkylene chain having between 8 and 18 carbon atoms, for example 8 and 16 carbon atoms, for example 8 and 14 carbon atoms, for example 9 and 15 carbon atoms, for example 10 carbon atoms. Preferably, R is a linear saturated alkylene chain having between 8 and 16 carbons, for example 10 carbon atoms. Herein alkylene means an alkane based di-radical, so has two points of attachment to the rest of the molecule.

R may be, for example, a quaternary amine according to formula (Ia), in which $R_a$ and $R_b$ are each a linear or branched saturated or unsaturated alkylene chain having between 8 and 18 carbon atoms, for example 8 and 16 carbon atoms, for example 8 and 14 carbon atoms, for example 9 and 15 carbon atoms, for example 10 carbon atoms. $R_a$ and $R_b$ may each be a linear or branched saturated alkylene chain having a different number of carbon atoms or the same number of carbon atoms.

Preferably, $R_a$ and $R_b$ are each a linear saturated alkylene chain having between 8 and 16 carbon atoms, for example 10 carbon atoms.

A saturated linear alkylene chain may be represented by the following formula:

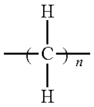

or

wherein n is the number of repeat units, that is the number of carbon atoms in the linear alkylene chain. Thus, in the case of R being an alkylene chain having between 8 and 20 carbon atoms, it is preferred that R is

n wherein n is between 8 and 16, for example 10. In the case of R being a quaternary amine having the formula (Ia) as set out above, it is preferred that $R_a$ and $R_b$ is

wherein n is between 8 and 16, for example 10.

In the case of, for example, R being an alkylene chain having 10 carbons, R may be represented by the following formula

.

A may, for example, comprise halide ions, such as chloride ($Cl^-$) ions, bromide ($Br^-$) ions, iodide ions ($I^-$) and/or fluoride ions ($F^-$). A may, for example, comprise ions of other organic and non-organic acids, such as sulphate ($SO_4^{2-}$), carbonate ($CO_3^{2-}$), hydrogen carbonate ($HCO_3^-$), hydrogen sulphate ($HSO_4^-$) acetate ions ($CH_3COO^-$) and/or formate ions ($HCOO^-$). In the case of R being an alkylene chain having between 8 and 20 carbon atoms, preferably A comprises two halide ions, for example two chloride ions, thus having a total charge of −2. In the case of R being a quaternary amine having formula (Ia) as set out above, preferably A comprises two chloride ions and a bromide ion, thus having a total charge of −3.

$R_1$, $R_2$, $R_3$, $R_4$, $R_5$ and $R_6$ may each independently be selected from $C_{1-4}$ alkyl and H, for example $R_1$, $R_2$, $R_3$, $R_4$, $R_5$ and $R_6$ may each be methyl. $R_E$ may be chloride, bromide, iodide, or fluoride. In the case of the ester oxygen being bonded to the aromatic ring of E at position 2 with respect to the methyl group, $R_E$ may be bonded to the aromatic ring at position 3, 5 or 6 with respect to the methyl group. In the case of the ester oxygen being bonded to the aromatic group of E at position 3 with respect to the methyl group, $R_E$ may be bonded to the aromatic ring at position 2, 5 or 6 with respect to the methyl group.

Preferably, the compound of formula (I) above has the following formula:

(II)

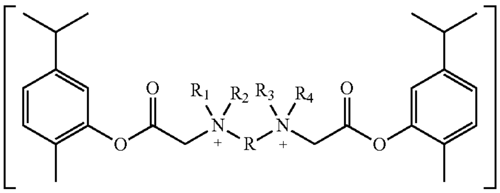

[A] or (III)

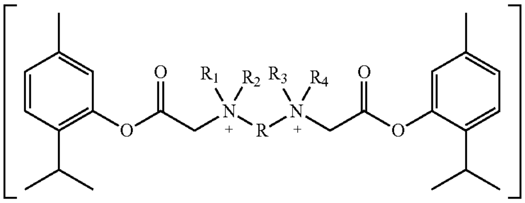

[A]

in which R, $R_1$, $R_2$, $R_3$, $R_4$ and A are as defined above for formula (I).

Preferably, the compound of formula (I) has the following formula:

(IV)

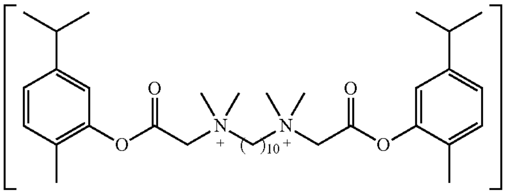

[$2Cl^-$]

-continued (V)

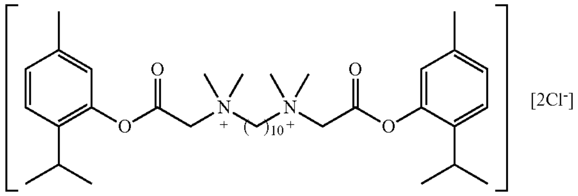

(VI)

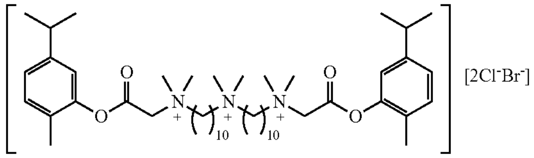

or (VII)

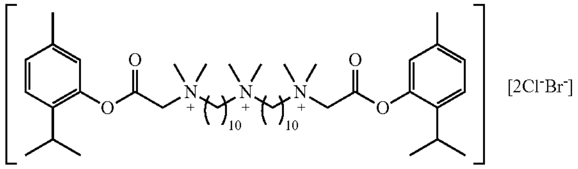

In formula IV and V, it will be appreciated that R is a linear saturated alkylene chain having 10 carbon atoms, and A is two chloride ions. In formula VI and VII, it will be appreciated that R is a quaternary amine, in which $R_a$ and $R_b$ are each saturated linear alkylene chains having 10 carbon atoms, and A is two chloride ions and one bromide ion. It will be appreciated that in formula IV and V, $R_1$, $R_2$, $R_3$ and $R_4$ are each methyl. It will be appreciated that in formula VI and VII, $R_1$, $R_2$, $R_3$, $R_4$, $R_5$ and $R_6$ are each methyl.

In another embodiment of the invention, there is provided a compound having the following formula:

(VIII)

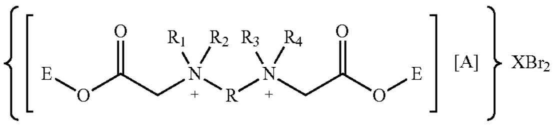

wherein R is an alkylene chain having between 8 and 20 carbon atoms, and A is one or more anions having a total charge of −2;

or R is a quaternary amine having the following formula:

(Ia)

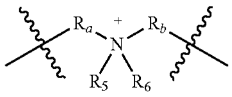

wherein $R_a$ and $R_b$ are each an alkylene chain having between 8 and 20 carbon atoms, and A is one or more anions having a total charge of −3;

$R_1$, $R_2$, $R_3$, $R_4$, $R_5$ and $R_6$ are each independently selected from $C_{1-10}$ alkyl and H;

E has the following formula (Ib)

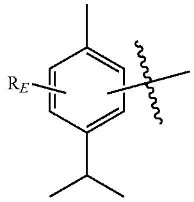

, wherein the ester oxygen is bonded to the aromatic ring of each E at the same position, the position being 2 or 3; wherein $R_E$ is H or a halide and wherein X is 2, 3, 4 or 6.

R may be, for example, a linear or branched saturated or unsaturated alkylene chain having between 8 and 18 carbon atoms, for example 8 and 16 carbon atoms, for example 8 and 14 carbon atoms, for example 9 and 15 carbon atoms, for example 10 carbon atoms. Preferably, R is a linear saturated alkylene chain having between 8 and 16 carbons, for examples 10 carbon atoms.

R may be, for example, a quaternary amine according to formula (Ia), in which $R_a$ and $R_b$ are each linear or branched saturated or unsaturated alkylene chains having between 8 and 18 carbon atoms, for example 8 and 16 carbon atoms, for example 8 and 14 carbon atoms, for example 9 and 15 carbon atoms, for example 10 carbon atoms. $R_a$ and $R_b$ may each be linear or branched saturated alkylene chains having a different number of carbon atoms or the same number of carbon atoms.

Preferably, $R_a$ and $R_b$ are each a linear saturated alkylene chain having between 8 and 16 carbon atoms, for example 10 carbon atoms.

A saturated linear alkylene chain may be represented by the following formula:

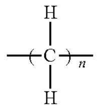

or

wherein n is the number of repeat units, that is the number of carbon atoms in the linear alkylene chain. Thus, in the case of R being an alkylene chain having between 8 and 20 carbon atoms, it is preferred that R is

wherein n is between 8 and 16, for example 10. In the case of R being a quaternary amine having the formula (Ia) as set out above, it is preferred that $R_a$ and $R_b$ is

wherein n is between 8 and 16, for example 10.

In the case of, for example, R being an alkylene having 10 carbons, R may be represented by the following formula

.

A may, for example, comprise halide ions, such as chloride ($Cl^-$) ions, bromide ($Br^-$) ions iodide ions ($I^-$) and/or fluoride ions ($F^-$). A may, for example comprise ions of other organic and non-organic acids, such as sulphate ($SO_4^{2-}$), carbonate ($CO_3^{2-}$), hydrogen carbonate ($HCO_3^-$), hydrogen sulphate ($HSO_4^-$), acetate ($CH_3COO^-$), and/or formate ions ($HCOO^-$). In the case of R being an alkylene chain having between 8 and 20 carbon atoms, preferably A comprises two halide ions, for example two chloride ions, thus having a total charge of −2. In the case of R being a quaternary amine having formula (Ia) as set out above, preferably A comprises two chloride ions and a bromide ion, thus having a total charge of −3.

$R_1$, $R_2$, $R_3$, $R_4$, $R_5$ and $R_6$ may each independently be selected from $C_{1-4}$ alkyl and H, for example $R_1$, $R_2$, $R_3$, $R_4$, $R_5$ and $R_6$ may each be methyl.

$R_E$ may be chloride, bromide, iodide, or fluoride. In the case of the ester oxygen being bonded to the aromatic ring of E at position 2 with respect to the methyl group, $R_E$ may be bonded to the aromatic ring at position 3, 5 or 6 with respect to the methyl group. In the case of the ester oxygen being bonded to the aromatic group of E at position 3 with respect to the methyl group, $R_E$ may be bonded to the aromatic ring at position 2, 5 or 6 with respect to the methyl group.

Preferably, the compound of formula (VIII) above has the following formula:

(IX)

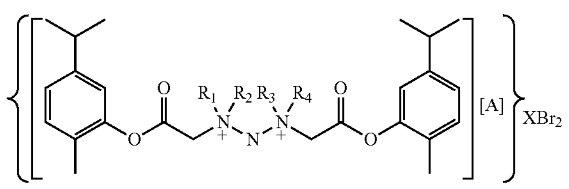

or (X)

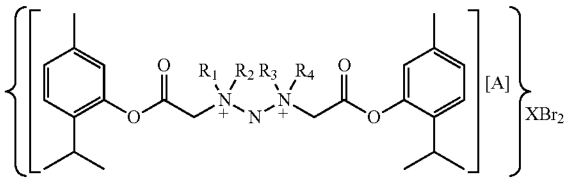

wherein R, $R_1$, $R_2$, $R_3$, $R_4$, X and A are as defined above for formula (IX).

Preferably, the compound of formula (VIII) has the following formula:

(XI)

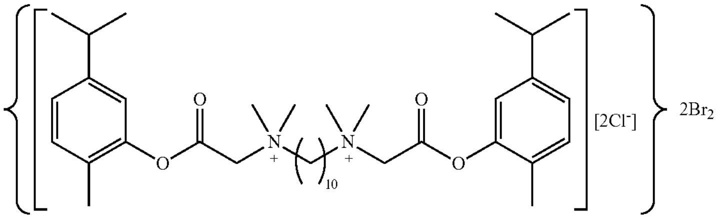

or (XII)

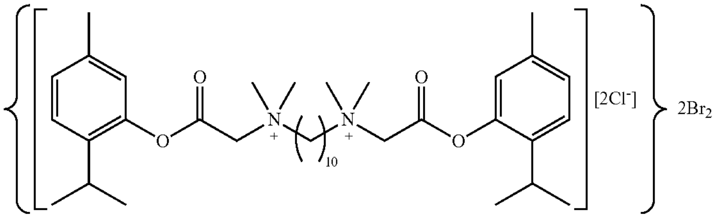

or (XIII)

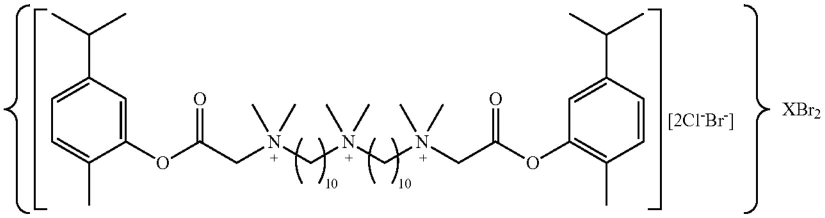

or (XIV)

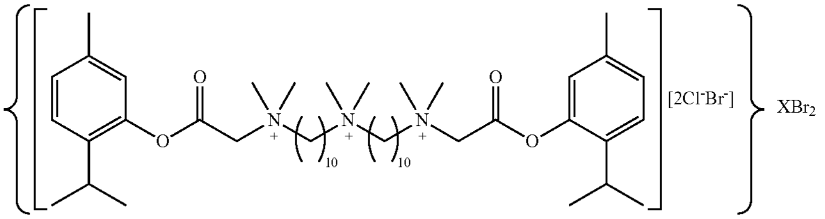

wherein X is 3 or 6.

In formula (XI) and (XII), it will be appreciated that R is a linear saturated alkylene chain having 10 carbon atoms; and A is two chloride ions.

In formula (XIII) and (XIV), it will be appreciated that R is a quaternary amine, in which $R_a$ and $R_b$ are each saturated linear alkylene chains having 10 carbon atoms, and A is two chloride ions and one bromide ion. It will be appreciated that in formula (XI) and (XII), $R_1$, $R_2$, $R_3$ and $R_4$ are each methyl. It will be appreciated that in formula (XIII) and (XIV), $R_1$, $R_2$, $R_3$, $R_4$, $R_5$ and $R_6$ are each methyl.

The applicant has found that the above compounds represented by formula I to XIV demonstrate surprising anti bacterial, antifungal and antiviral activity. Without being bound by any particular theory, it is hypothesised that this antibacterial and antifungal activity may stem from the combination of the aromatic thymol and carvacrol groups, quaternary ammonia groups and long chain alkyl groups. Additionally, complexing compounds according to formulae I-IV with bromine may further increase their antibacterial and antifungal properties.

The applicant has found that the compounds represented by formulas I to XIV demonstrate enhanced antibacterial, antifungal and antiviral activity over similar compounds in which the ester oxygen is bonded to the aromatic ring of each group E at different positions.

In another aspect of the invention, there is provided a pharmaceutical composition (for example a human pharmaceutical composition and/or a veterinary pharmaceutical composition), comprising a compound according to formulae (I) to (XIV) above.

The pharmaceutical composition may be in a form suitable for one or more of oral, rectal, parenteral, transdermal, intravenous, intra-arterial, intraosseous infusion, intracerebral, intracerebroventricular, intrathecal, intramuscular, subcutaneous, intravaginal, intraperitoneal, epidural, intracerebral, intraosseous infusion, intravitreal, transmucosal, buccal, or nasal administration.

The pharmaceutical composition may comprise a compound according to formulae (1) to (XIV), a pharmaceutically acceptable carrier, such as aqueous solution, non-toxic excipients, including salts and preservatives, buffers and the like.

Examples of suitable aqueous and non-aqueous pharmaceutical carriers, diluents, solvents or vehicles include water, ethanol, polyols (such as glycerol, propylene glycol, polyethylene glycol, and the like), carboxymethylcellulose and suitable mixtures thereof, vegetable oils (such as olive oil), and injectable organic esters such as ethyl oleate.

Examples of pharmaceutically acceptable excipients include antiadherents, binders, coatings, colourings, disintegrant, flavourings, glidants, lubricants, preservatives, sorbents and sweeteners.

The pharmaceutical compositions of the present invention may also contain additives such as but not limited to preservatives, wetting agents, emulsifying agents, surfactants and dispersing agents. Antibacterial and antifungal agents can be included to prevent growth of microbes and includes, for example, m-cresol, benzyl alcohol, paraben, chlorobutanol, phenol, sorbic acid, and the like. If a preservative is included, benzyl alcohol, phenol and/or m-cresol are preferred; however, the preservative is by no means limited to these examples. Furthermore, it may be desirable to include isotonic agents such as sugars, sodium chloride, and the like.

A pharmaceutical composition suitable for oral administration may be in the form of, for example, a tablet, a pill, a sugar coated agent, a powder, a capsule, a liquid, a gel, a syrup, a slurry, a suspension, a cachet and the like. The composition may comprise a pharmaceutically acceptable carrier, for example liposomes, lactose, trehalose, sucrose, mannitol, xylitol, crystalline cellulose, chitosan, calcium carbonate, talc, titanium oxide, silica and the like.

The pharmaceutical composition may be obtained, for example, by combining the compounds of the invention with a solid excipient, pulverizing the mixture (if necessary) and inserting into a capsule, for example, a soft sealed capsule consisting of a gelatin capsule, gelatin and coating (e.g., glycerol or sorbitol) or a capsule composition suitable for vegetarians. In the soft capsule, the composition may be dissolved or suspended in an appropriate liquid, such as a fatty oil, liquid paraffin or liquid polyethylene glycol, with or without a stabilizer.

In a further aspect of the present invention there is provided a compound or a pharmaceutical composition as set out above for use as a medicament.

In a further aspect of the present invention there is provided a compound or a pharmaceutical composition as set out above for use in the treatment of Herpes virus, Human Papilloma Virus, bacterial infections and/or fungal infections.

The Herpes virus may be one or more of a Herpes Simplex virus, Herpes Simplex virus 1 (HSV-1), Herpes Simplex virus 2 (HSV-2), Varicella zoster virus (VZV), Epstein-Barr virus, Cytomegalovirus, Human Cytomegalovirus, Roseolovirus, Kaposi's Sarcoma-associated herpesvirus, animal Herpesviruses, such as Pseudorabies virus, and Bovine herpesvirus 1.

Preferably, the Herpes virus is a Herpes Simplex virus (for example Herpes Simplex virus 1 or Herpes Simplex virus 2) or Cytomegalovirus.

The bacterial infections may include those caused by gram positive and/or gram negative bacteria.

The bacterial infections may be caused by, for example, *Staphylococcus aureus, Escherichia coli, Pseudomonas aeruginosa* and/or *Salmonella enterica* bacteria.

The fungal infections may be superficial mycoses, cutaneous mycoses, subcutaneous mycoses, and/or systemic mycoses.

The fungal infections may be caused by, for example, *Candida albicans.*

In a further aspect of the invention, there is provided the use of a compound or pharmaceutical composition as set out above in the manufacture of a medicament for treating Herpes virus, Human Papilloma Virus, bacterial infections and/or fungal infections.

The herpes virus may be one or more of a Herpes Simplex virus, Herpes Simplex virus 1 (HSV-1), Herpes Simplex virus 2 (HSV-2), Varicella zoster virus (VZV), Epstein-Barr virus, Cytomegalovirus, Human Cytomegalovirus, Roseolovirus, Kaposi's Sarcoma-associated herpesvirus, animal Herpesviruses, such as Pseudorabies virus, and Bovine Herpesvirus 1.

Preferably, the Herpes virus is a Herpes Simplex virus (for example Herpes Simplex virus 1 or Herpes Simplex virus 2) or Cytomegalovirus.

The bacterial infections may include those caused by gram positive and/or gram negative bacteria.

The bacterial infections may be caused by, for example, *Staphylococcus aureus, Escherichia coli, Pseudomonas aeruginosa* and/or *Salmonella enterica* bacteria.

The fungal infections may be superficial mycoses, cutaneous mycoses, subcutaneous mycoses, and/or systemic mycoses.

The fungal infections may be caused by, for example, *Candida albicans.*

In a further aspect of the invention, there is provided a method of treatment of Herpes virus, Human Papilloma Virus, bacterial infections and/or fungal infections, comprising a step of administering to a subject a compound or pharmaceutical composition as set out above.

The herpes virus may be one or more of a Herpes Simplex virus, Herpes Simplex virus 1 (HSV-1), Herpes Simplex virus 2 (HSV-2), Varicella zoster virus (VZV), Epstein-Barr virus, Cytomegalovirus, Human Cytomegalovirus, Roseolovirus, Kaposi's Sarcoma-associated Herpesvirus, animal Herpesviruses, such as Pseudorabies virus, and Bovine Herpesvirus 1.

Preferably, the herpes virus is a Herpes Simplex virus (for example Herpes Simplex virus 1 or Herpes Simplex virus 2) or Cytomegalovirus.

The bacterial infections may include those caused by gram positive and/or gram negative bacteria.

The bacterial infections may be caused by, for example, *Staphylococcus aureus, Escherichia coli, Pseudomonas aeruginosa* and/or *Salmonella enterica* bacteria.

The fungal infections may be superficial mycoses, cutaneous mycoses, subcutaneous mycoses, and/or systemic mycoses.

The fungal infections may be caused by, for example, *Candida albicans.*

In a further aspect of the present invention, there is provided a process for producing the compound according to formula (I) comprising the following steps:

i) reacting a compound having the formula (XV)

(XV)

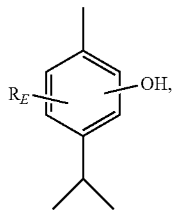

wherein the alcohol group is bonded to the benzene ring in position 2 or 3 and wherein $R_E$ is H or halide, with $R_7CH_2COCl$ to form a compound having the formula (XVI):

(XVI)

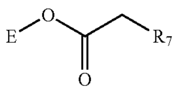

wherein $R_7$ is chloride or bromide, E is (Ib)

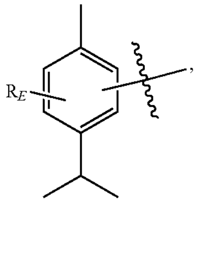

wherein the ester oxygen is bonded to the aromatic ring of E at position 2 or 3, and $R_E$ is H or halide; and ii) reacting 1 molar equivalents of the compound having the formula (XVII)

(XVII)

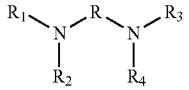

with 2 molar equivalent of the compound having formula (XVI) to form a compound having the formula (I)

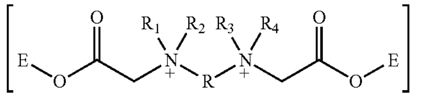

wherein R is an alkylene chain having between 8 and 20 carbon atoms, and A is one or more anions having a total charge of −2;

or R is a quaternary amine having the following formula:

(Ia)

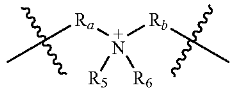

wherein $R_a$ and $R_b$ are each an alkylene chain having between 8 and 20 carbon atoms, and A is one or more anions having a total charge of −3;

E has the following formula (Ib)

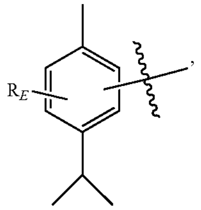

wherein the ester oxygen is bonded to the aromatic ring of each E at the same position, the position being position 2 or 3, and $R_E$ is H or halide;

$R_1$, $R_2$, $R_3$, $R_4$, $R_5$ and $R_6$ are each independently selected from $C_{1-10}$ alkyl and H.

The reactions of step ii may be carried out in acetonitrile as solvent.

In the case of R being an alkylene chain having between 8 and 20 carbon atoms, the process may include an additional step of reacting a compound having the formula (XVIII)

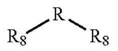

with two molar equivalents of a compound having the formula (XIX)

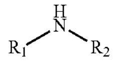

to form a di tertiary amine having the following formula (XVII)

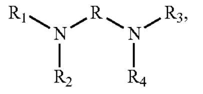

wherein $R_3$ and $R_4$ are the same as $R_1$ and $R_2$, and $R_1$ and $R_2$ are each independently selected from $C_{1-10}$ alkyl and H;

wherein $R_a$ is a halide, for example bromide or chloride; and R is an alkylene chain having between 8 and 20 carbon atoms.

In the case of R being a quaternary amine having the following formula:

(Ia)

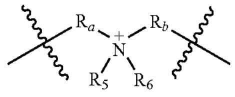

wherein $R_a$ and $R_b$ are each an alkylene chain having between 8 and 20 carbon atoms, and $R_5$ and $R_6$ are each independently selected from $C_{1-10}$ alkyl and H, the process may include an additional step of reacting a 2 molar equivalents of a compound having the formula (XVIII)

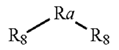

with three molar equivalents of (XIX)

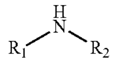

to form a quaternary amine having the following formula (XVIIa)

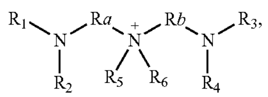

wherein Ra is an alkylene chain having between 8 and 20 carbon atoms, $R_a$ is a halide, for example bromine or chlorine, $R_a$ and $R_b$ are the same and are each an alkylene chain having between 8 and 20 carbon atoms, $R_1$, $R_2$, $R_3$, $R_4$, $R_5$ and $R_6$ are the same and are selected from $C_{1-10}$ alkyl and H.

The reactions in step i may both take place at a temperature of −10° C.

The process may further comprise one or more steps of separation and or extraction, for example a separation step may include column chromatography, low pressure liquid chromatography, high performance liquid chromatography and the like. Purification steps may include standard purification processes known in the art, for example, filtration, evaporation, liquid-liquid extraction, crystallisation, adsorption, recrystallization, chromatography, distillation and the like.

In a further aspect of the present invention there is provided a process for the production of a compound according formula (VIII) comprising reacting the compound having formula (I)

(I)

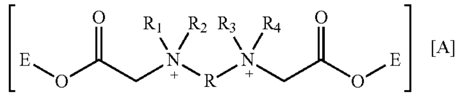

with bromine to form a compound having formula (VIII)

(VIII)

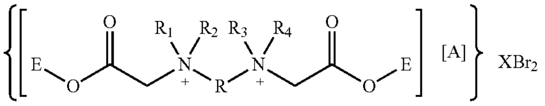

wherein R is an alkylene chain having between 8 and 20 carbon atoms, and A is one or more anions having a total charge of −2, or R is a quaternary amine having the following formula:

(Ia)

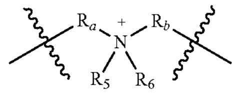

wherein $R_a$ and $R_b$ are each an alkylene chain having between 8 and 20 carbon atoms, and A is one or more anions having a total charge of −3;

$R_1$, $R_2$, $R_3$, $R_4$, $R_5$ and $R_6$ are each independently selected from $C_{1-10}$ alkyl and H; E and has the following formula (Ib)

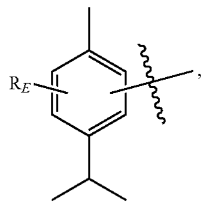

wherein the ester oxygen is bonded to the aromatic ring of each E at the same position, the position being 2 or 3; $R_E$ is H or halide;

and wherein X is 2, 4, 3 or 6.

The present invention will now be described with reference to the following examples.

EXAMPLE 1

Synthesis of the compound of formula (IV)

(IV)

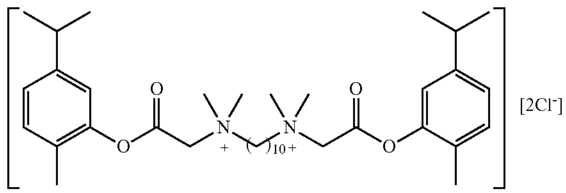

Separation steps may include steps of performing column chromatography, low pressure liquid chromatography, high performance liquid chromatography and the like. Purification steps may include standard purification processes known in the art, for example, filtration, evaporation, liquid-liquid extraction, crystallisation, adsorption, recrystallization, chromatography, distillation and the like.

The compound of formula (IV) has the following systematic name, formula and molecular weight:

Systematic name:N1,N10-bis(2-(5-isopropyl-2-methylphenoxy)-2-oxoethyl)-N1,N1,N10,N10-tetramethyldecane-1,10-diaminium dichloride Formula:$C_{38}H_{62}N_2O_4^{+2}$ $2Cl^-$ Molecular weight: 681.81

Scheme 1

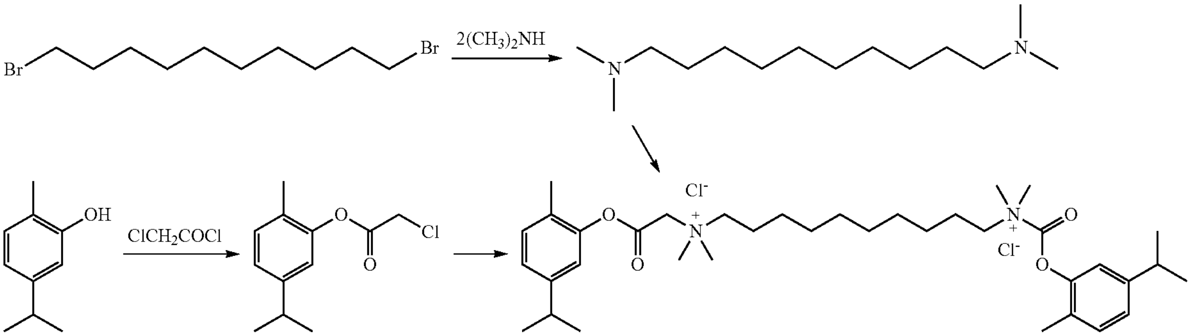

In a first step, 1,10-dibromodecane is reacted with 2 molar equivalents of dimethylamine to form 1,10-Bis(dimethylamino)decane. The reaction takes place at 4-5° C. in a suitable solvent such as benzene, diethyl ether or dimethylamine and is followed by a step of acid extraction followed by alkaline treatment and extraction with diethyl ether. The extracted fractions are dried over magnesium sulphate and then purified by vacuum distillation.

In a second step, Carvacrol (2-Methyl-5-(1-methylethyl)-phenol) is reacted with chloroacetyl chloride. The reaction is carried out at −10° C. for 1 hour and then stirred at room temperature for 12 hours. The reaction mixture is then washed with acid, followed by treatment with sodium bicarbonate and then water. The organic layer is dried over sodium sulphate, filtered and the solvent is removed under vacuum.

In a third step, 2 molar equivalents of the compound formed in the second step is reacted with one molar equivalent of 1,10-Bis(dimethylamino)decane to form the compound of formula (IV). The reaction in the third step is carried out using an appropriate solvent such as acetonitrile and the reaction mixture is stirred for 24 hours.

It will be appreciated that further purification and separation steps may also be included in the process, for example between each of the above steps and also after the process is complete to purify the final compound having formula (IV).

EXAMPLE 2

Synthesis of the Compound of Formula (V)

(V)

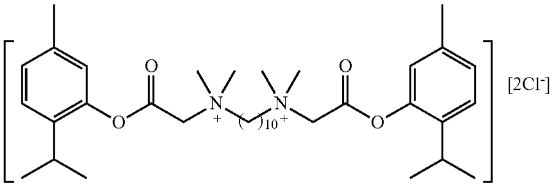

In a first step, 1,10-dibromodecane is reacted with 2 molar equivalents of dimethylamine to form 1,10-Bis(dimethylamino)decane. The reaction takes place at 4-5° C. in benzene in a suitable solvent such as benzene, diethyl ether or dimethylamine and is followed by a step of acid extraction followed by alkaline treatment and extraction with diethyl ether. The extracted fractions are dried over magnesium sulphate and then purified by vacuum distillation.

In a second step, thymol (2-isopropyl-5-methylphenol) is reacted with chloroacetyl chloride. The reaction is carried out at −10° C. for 1 hour and then stirred at room temperature for 12 hours. The reaction mixture is then washed with acid, followed by treatment with sodium bicarbonate and then water. The organic layer is dried over sodium sulphate, filtered and the solvent is removed under vacuum.

In a third step, 2 molar equivalents of the compound formed in the second step is reacted with one molar equivalent of 1,10-Bis(dimethylamino)decane to form the compound of formula (V). The reaction in the third step is carried out using an appropriate solvent such as acetonitrile and the reaction mixture is stirred for 24 hours.

It will be appreciated that further purification and separation steps may also be included in the process, for example between each of the above steps and also after the process is complete to purify the final compound having formula (V).

Separation steps may include steps of performing column chromatography, low pressure liquid chromatography, high performance liquid chromatography and the like. Purification steps may include standard purification processes known in the art, for example, filtration, evaporation, liquid-liquid extraction, crystallisation, adsorption, recrystallization, chromatography, distillation and the like.

Systematic Name:N1,N10-bis(2-(2-isopropyl-5-methylphenoxy)-2-oxoethyl)-N1,N1,N10,N10-tetramethyldecane-1,10-diaminium dichloride Formula:$C_{38}H_{62}N_2O_4{}^{+2}2Cl^-$ Molecular Weight: 681.81

Scheme 2

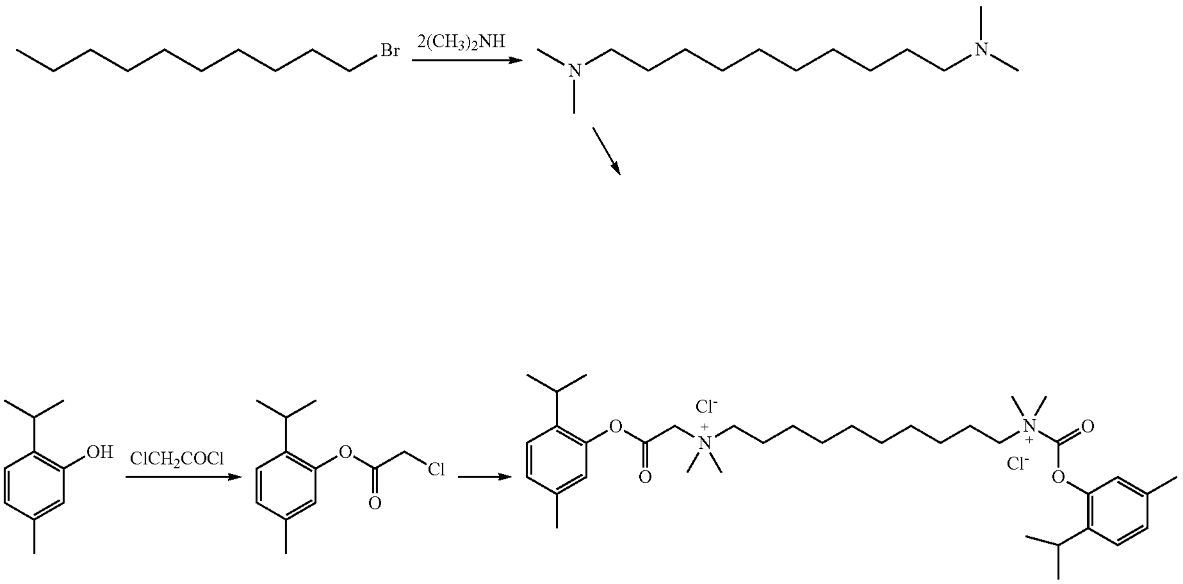

EXAMPLE 3

Synthesis of the Compound of Formula (VI)

(VI)

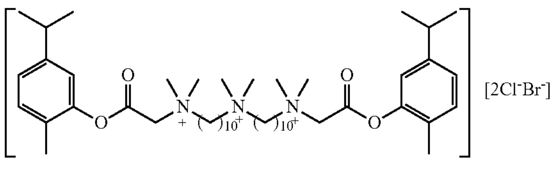

In a first step, 2 molar equivalents of 1,10-Dibromodecane are reacted with 3 molar equivalents of dimethylamine. The reaction takes place at 4-5° C. in a suitable solvent such as benzene or diethyl ether and is followed by a step of acid extraction followed by alkaline treatment and extraction with diethyl ether. The extracted fractions are dried over magnesium sulphate and then purified by vacuum distillation.

In a second step, carvacrol (2-Methyl-5-(1-methylethyl)-phenol) is reacted with chloroacetyl chloride. The reaction is carried out at −10° C. for 1 hour and then stirred at room temperature for 12 hours. The reaction mixture is then washed with acid, followed by treatment with sodium bicarbonate and then water. The organic layer is dried over sodium sulphate, filtered and the solvent is removed under vacuum.

In a third step, one molar equivalent of the compound formed in step 1 is reacted with the 2 molar equivalents of the compound formed in step 2 to form the compound having formula (VI). The reaction in the third step is carried out using an appropriate solvent such as acetonitrile and the reaction mixture is stirred for 24 hours.

It will be appreciated that further purification and separation steps may also be included in the process, for example between each of the above steps and also after the process is complete to purify the final compound having formula (VI).

Separation steps may include steps of performing column chromatography, low pressure liquid chromatography, high performance liquid chromatography and the like. Purification steps may include standard purification processes known in the art, for example, filtration, evaporation, liquid-liquid extraction, crystallisation, adsorption, recrystallization, chromatography, distillation and the like.

Systematic Name:N1-(2-(5-isopropyl-2-methylphenoxy)-2-oxoethyl)-N10-(10-((2-(5-isopropyl-2-methylphenoxy)-2-oxoethyl)dimethylammonio)decyl)-N1,N1,N10,N10-tetramethyldecane-1,10-diaminium bromide dichloride Formula:$C_{50}H_{88}N_3O_4{}^{+3}Br2Cl^-$ Molecular Weight: 946.06

Scheme 3

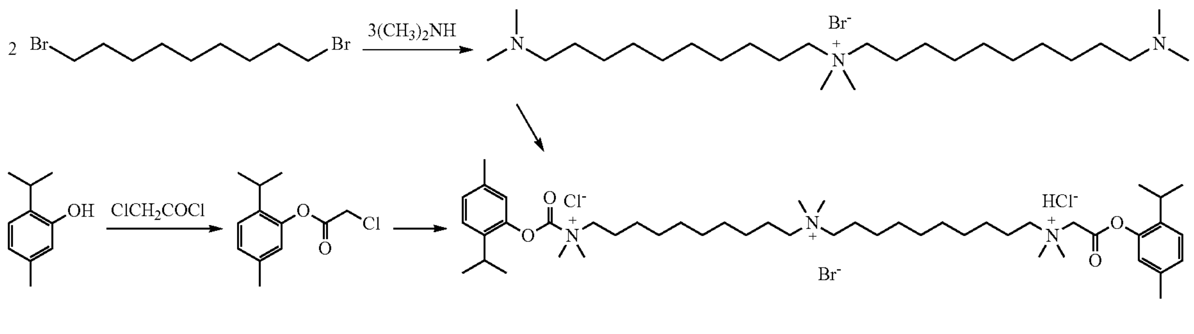

EXAMPLE 4

Synthesis of the Compound of Formula (VII)

(VII)

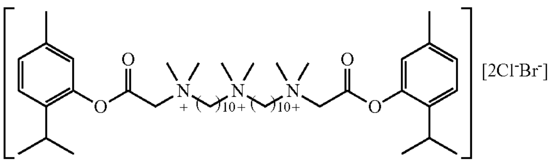

In a first step, 2 molar equivalents of 1,10-Dibromodecane are reacted with 3 molar equivalents of dimethylamine The reaction takes place at 4-5° C. in a suitable solvent such as benzene or diethyl ether and is followed by a step of acid extraction followed by alkaline treatment and extraction with diethyl ether. The extracted fractions are dried over magnesium sulphate and then purified by vacuum distillation.

In a second step, thymol (2-isopropyl-5-methylphenol) is reacted with chloroacetyl chloride. The reaction is carried out at −10° C. for 1 hour and then stirred at room temperature for 12 hours. The reaction mixture is then washed with acid, followed by treatment with sodium bicarbonate and then water. The organic layer is dried over sodium sulphate, filtered and the solvent is removed under vacuum.

In a third step, one molar equivalent of the compound formed in step 1 is reacted with the 2 molar equivalents of the compound formed in step 2 to form the compound having formula (VII). The reaction in the third step is carried out using an appropriate solvent such as acetonitrile and the reaction mixture is stirred for 24 hours.

It will be appreciated that further purification and separation steps may also be included in the process, for example between each of the above steps and also after the process is complete to purify the final compound having formula (VII).

Separation steps may include steps of performing column chromatography, low pressure liquid chromatography, high performance liquid chromatography and the like. Purification steps may include standard purification processes known in the art, for example, filtration, evaporation, liquid-liquid extraction, crystallisation, adsorption, recrystallization, chromatography, distillation and the like.

Systematic Name:N1-(2-(2-isopropyl-5-methylphenoxy)-2-oxoethyl)-N10-(10-((2-(2-isopropyl-5-methylphenoxy)-2-oxoethyl)dimethylammonio)decyl)-N1,N1,N10,N10-tetramethyldecane-1,10-diaminium bromide dichloride Formula:$C_{50}H_{88}N_3O_4^{+3}Br2Cl^-$ Molecular Weight: 946.06

Scheme 4

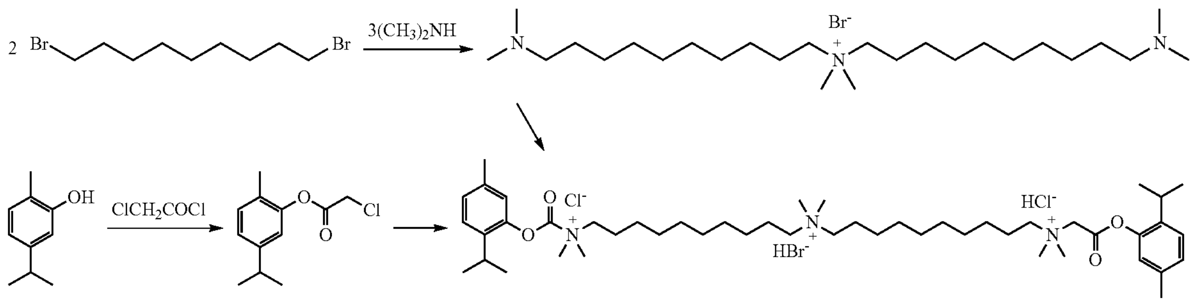

It will be appreciated that to synthesis the Bromine complexes defined by formula XI to XIV, the compounds of formula IV to VII are treated with bromine to form the complexes of formulas XI to XIV. It will be appreciated that further purification and separation steps may also be included in this process.

EXAMPLE 5

Minimum Inhibitory Concentration (MIC) Determination by Broth Micro Dilution

Equipment

McFarland standard 0.5

Falcon round-bottom 5 ml tubes
Disposable loops (1 μl and 10 μl)
Pipettes tips (0.5 μl-1000 μl)
Tissue Culture plate, 96 well
Multichannel micropipettes (5-50 μl),(30-300 μl)
Disposable Petri dishes
Disposable reagent reservoirs Media
Sterile normal saline
TSB (Tryptic Soy Broth)
TSA (Tryptic Soy Agar)
0,02% resazurin sterile solution
Bacterial strains
*Staphylococcus aureus* ATCC-6538
*Escherichia coli* A TCC-8739

Procedure
Standardisation of Inoculum

From a pure o/n culture, material from at least 3-4 colonies was chosen and suspended totally in 2 ml saline in tubes. The suspensions were mixed. The inoculums were standardized according to the scale of 0.5 MacFarland (dilution factor 1:10, sterile saline solution) to obtain the final concentration of $1.5\times10^4$ cfu/ml. The inoculums were 30 mixed. The suspension was used for inoculation within 15 minutes.

Inoculation and Incubation

Each sample was dissolved in an appropriate solvent (water/96% ethanol) to a concentration of 5000 μg/ml. Using the method of serial dilutions, the concentration of the initial solution was adjusted to 625 μg/ml for gram negative bacteria and 78 μg/ml for gram positive bacteria. For fungi, the working concentration was 1250 μg/ml.

revealed by the addition of resazurin sterile solution (20 μl, 0.02%, w/v) and re-incubation for 3 hours. Minimum inhibitory concentration (MIC), which is defined as the lowest concentration of sample capable of inhibiting the growth of microorganisms, was determined by the permanence of blue coloration in the wells. A change of color from blue to red (due to the reduction of dye) indicated bacterial growth. The wells that showed no apparent growth were selected to evaluate the MIC, which was determined by the absence of microbial growth on plates containing TSB.

The Results of these Experiments are Set Out Below in the Following Tables.

*Staphylococcus aureus* ATCC 6538 $4.5\times10^3$ Cfu/Ml

TABLE 1

| Compound | MIC/μg/mL |
|---|---|
| Comparative compound 1 | 1.95 |
| Formula VII | 0.98 |

*Escherichia coli* ATCC-8739 $6.5\times10^3$ Cfu/ml

TABLE 2

| Compound | MIC/μg/mL |
|---|---|
| Comparative compound 1 | 7.8 |
| Formula VII | 3.9 |

TABLE 3

| Compound | Structure |
|---|---|
| Comparative Compound 1 | 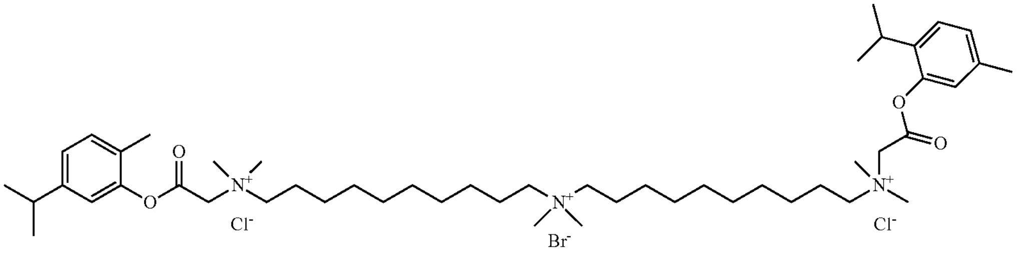 [SMILES: Cc1ccc(C(C)C)c(OC(=O)C[N+](C)(C)CCCCCCCCCC[N+](C)(C)CCCCCCCCCC[N+](C)(C)CC(=O)Oc2cc(C(C)C)ccc2C)c1 ; [Cl-] ; [Cl-] ; [Br-]] |
| Formula VII | 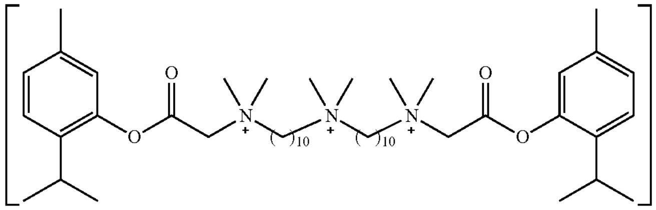 [2Cl⁻Br⁻] |

The tests were performed in 96 well plates, in which each well received 100 μl of sterile TSB.

100 μl of the initial concentration of the sample was added to the first well. Serial dilutions were made by transferring 100 μl from each previous well to the subsequent one (dilution factor 1:1). In each well, 20 μl of the inoculum is added. Each well had a final volume of 120 μl.

The microbial growth, sterility of the medium and the solvent were controlled simultaneously. The plates were incubated at 37±1° C., for 24 h for bacteria and at 34±1° C., for 48 h for yeasts. The inhibition of growth of bacteria was

EXAMPLE 6

MIC Determination by Broth Micro Dilution
Equipment
McFarland standard 0.5
Falcon round-bottom 5 ml tubes
Disposable loops (1 μl and 10 μl)
Pipettes tips (0.5 μl-1000 μl)
Tissue Culture plate, 96well
Multichannel micropipettes (5-50 μl),(30-300 μl)
Disposable Petri dishes Disposable reagent reservoirs Media Sterile normal saline TSB (Tryptic Soy Broth)

TSA (Tryptic Soy Agar)

0,02% resazurin sterile solution

Bacterial strains

*Staphylococcus aureus* ATCC-6538

*Escherichia coli* A TCC-8739

*Pseudomonas aeruginosa* ATCC-9027

*Candida albicans* ATCC-10231

*Candida albicans* NCTC-885-653

*Saccharomyces cerevisiae* ATCC-9763

*Salmonella enterica* serovar *Typhimurium* ATCC 14028

*Saccharomyces cerevisiae* ATCC-2601

Procedure

Standardisation of Inoculum

From a pure o/n culture, material from at least 3-4 colonies was chosen. The material was suspended totally in 2 ml saline in tubes and mixed.

The inoculums were standardized according to the scale of 0.5 MacFarland (dilution factor 1:10, sterile saline solution) to obtain the final concentration of $1.5\times10^4$cfu/ml. The inoculums were mixed. The suspension was used for inoculation within 15 minutes.

Inoculation and Incubation

Each sample was dissolved in an appropriate solvent (water/96% ethanol) to a concentration of 5000 μg/ml. Using the method of serial dilutions, the concentration of the initial solution was adjusted to 625 μg/ml for gram negative bacteria and 78 μg/ml for gram positive bacteria. For fungi the working concentration was 1250 μg/ml.

The tests were performed in 96 well plates, in which each well received 100 μl of sterile TSB. 100 μl of the initial concentration was added to the first well. Serial dilutions were made by transferring 100 μl from each previous well to the subsequent one (dilution factor 1:1). In each well 20 μl of the inoculum was added. Each well had a final volume of 120 μl. The microbial growth, sterility of the medium and the solvent were controlled simultaneously. The plates were incubated at 37 t 1° C., for 24 hours for bacteria and at 34±1° C., for 48 hours for yeasts. The inhibition of growth of bacteria was revealed by the addition of resazurin sterile solution (20 μl, 0.02%, w/v) and re-incubation for 3 h.

MIC, which is defined as the lowest concentration of sample capable of inhibiting the growth of microorganisms, was determined by the permanence of blue coloration in the wells. A change of color from blue to red (due to the reduction of dye) indicated the bacterial growth. The wells that showed no apparent growth were selected to evaluate the MIC, which was determined by the absence of microbial growth on plates containing TSB.

The Results of these Experiments are Set Out in the Following Tables.

*Escherichia coli* ATCC-8739 $1.7\times10^4$ Cfu/ml

TABLE 4

| Compound | MIC/μg/mL |
|---|---|
| Comparative compound 2 | 7.8 |
| Formula V | 3.9 |
| Formula IV | 3.9 |
| Vancomycin | 78 |

*Salmonella enterica* serovar *Typhimurium* ATCC 14028 $1.3\times10^4$ Cfu/ml

TABLE 5

| Compound | MIC/μg/mL |
|---|---|
| Comparative compound 2 | 7.8 |
| Formula IV | 3.9 |
| Vancomycin | 78 |

*Escherichia coli* ATCC-8739 $6.6\times10^3$ Cfu/ml

TABLE 6

| Compound | MIC/μg/mL |
|---|---|
| Comparative compound 2 | 7.8 |
| Formula V | 3.9 |

*Pseudomonas aeruginosa* ATCC-9027 $1.9\times10^4$ Cfu/ml

TABLE 7

| Compound | MIC/μg/mL |
|---|---|
| Comparative compound 2 | 7.8 |
| Formula V | 3.9 |

*Escherichia coli* ATCC-8739 $4.1\times10^3$ Cfu/ml

TABLE 8

| Compound | MIC/μg/mL |
|---|---|
| Comparative compound 2 | 3.9 |
| Formula V | 1.95 |
| Formula IV | 1.95 |

*Pseudomonas aeruginosa* ATCC-9027 $4.7\times10^3$ Cfu/ml

TABLE 9

| Compound | MIC/μg/mL |
|---|---|
| Comparative compound 2 | 1.95 |
| Formula IV | 0.98 |

TABLE 10

| | MIC/μg/mL | | |
|---|---|---|---|
| | Comparative compound 2 | Formula V | Formula IV |
| *Candida albicans* ATCC 10231 | 15.6 | 3.9-7.8 | 3.9-7.8 |

TABLE 11

| | Comparative compound 2 | Formula V |
|---|---|---|
| *Candida albicans* NCTC 885-653 | 15.6 | 3.9-7.8 |

TABLE 12

| Compound | MIC/μg/mL |
|---|---|
| Comparative compound 2 | 1.95 |
| Formula V | 0.98 |

*Escherichia coli* ATCC-8739 $6.5\times10^3$ Cfu/ml

TABLE 13

| Compound | MIC/μg/mL |
|---|---|
| Comparative compound 2 | 7.8 |
| Formula V | 3.9 |
| Comparative compound 3 | 7.8 |
| Formula XI | 3.9 |

*Salmonella enterica* serovar *Typhimurium* ATCC 14028 (log 4 conditions)

TABLE 14

| Compound | MIC/mKg/mL |
|---|---|
| Comparative compound 2 | 7.8 |
| Formula IV | 3.9 |

*Escherichia coli* ATCC-8739 (log 4 conditions)

TABLE 15

| Compound | MIC/μg/mL |
|---|---|
| Comparative compound 2 | 7.8 |
| Formula V | 3.9 |
| Formula IV | 3.9 |

*Pseudomonas aeruginosa* ATCC-9027 (Log 4 conditions)

TABLE 16

| Compound | MIC/μg/mL |
|---|---|
| Comparative compound 3 | 7.8 |
| Formula XI | 3.9 |

The means of MIC for different isomers (μg/ml) were tested against various fungal strains that were clinical isolate resistant or sensitive to Fluconazole and Voriconazole (resistance indicated for more than 20 fungal generations, cultivated in the presence of Fluconazole or Voriconazole).

MIC values for Voriconazole and Fluconazole for all tested strains were 255 μg/ml and 511 μg/ml respectively.

*Candida albicans* ATCC-10231 Voriconazole resistant (20 G)

TABLE 17

| Compound | MIC/μg/mL |
|---|---|
| Comparative compound 2 | 7.8 |
| Formula V | 3.9 |

*Candida albicans* ATCC-10231 Fluconazole resistant (20 G)

| Compound | MIC/μg/mL |
|---|---|
| Comparative compound 2 | 15.6 |
| Formula V | 7.8 |

*Candida albicans* NTCT-885-653 Voriconazole resistant (20 G)

TABLE 18

| Compound | MIC/μg/mL |
|---|---|
| Comparative compound 2 | 1.95 |
| Formula V | 0.98 |

*Saccharomyces cerevisiae* ATCC-9763 Fluconazole resistant (20 G)

TABLE 19

| Compound | MIC/μg/mL |
|---|---|
| Comparative compound 2 | 3.9 |
| Formula IV | 0.98 |

*Saccharomyces cerevisiae* ATCC-2601 Fluconazole resistant (20 G)

TABLE 20

| Compound | MIC/μg/mL |
|---|---|
| Comparative compound 2 | 1.95 |
| Formula IV | 0.98 |
| Formula V | 0.98 |

EXAMPLE 7

Antiviral Activity

MRC5 cells were seeded in 96 well plates at a density of 20,000 cells/well and cultured at 37° C. under 5% $CO_2$ overnight. The next day, a medium containing serially diluted compounds and the virus were added to the wells. The resulting cultures were incubated at 37° C. and under 5% $CO_2$. Four days post infection, the medium was replenished. Seven days post infection, fluorescence intensity was determined using Acumen Cellista. Antiviral activity of the compounds was calculated based on the inhibition of expression of GFP at each concentration normalized by the cell control. Cytotoxicity of the compounds was assessed under the same conditions, but without virus infection, in parallel. Cell viability was measured with CCK8 following the manufacturer's manual.

Antiviral activity and cytotoxicity of the compounds was expressed as % Inhibition and % Viability, respectively, and calculated with the formulas below:

$$\text{Inhibition (\%)}=100-(\textit{Raw}\text{ data }\textit{CPD}-\text{Average}\textit{CC})/(\text{Average}\textit{VC}-\text{Average}\textit{CC})*100$$

$$\text{Viability (\%)}=(\textit{Raw}\text{ data }\textit{CPD}-\text{Average}\textit{MC})/(\text{Average}\textit{CC}-\text{Average}\textit{MC})*100$$

Raw data CPD indicates the values of the compound-treated wells; Average VC, Average CC and Average MC indicate the average values of the virus control, cell control and medium control wells, respectively.

EC50 and CC50 values were calculated using the GraphPad Prism software.

TABLE 21

| Virus | Cell line | Compound treatment duration | Detection reagent |
|---|---|---|---|
| US3-6-EGFP-HCMV-AD169 | MRC5 | 7/Fluorometry | GFP, CCK8 |

The results of the experiments are set out below in table 22.

TABLE 22

| Compound | $EC_{50}$ (μg/ml) | $CC_{50}$ (μg/ml) | SI ($CC_{50}/EC_{50}$) |
|---|---|---|---|
| Comparative compound 2 | 41.47 | >120.00 | >2.89 |
| Formula IV | 32.75 | >120.00 | >3.66 |
| Comparative compound 3 | 18.94 | 23.45 | 1.24 |
| Formula XI | 15.76 | 32.92 | 2.09 |

TABLE 23

| Compound | Structure |
|---|---|
| Comparative compound 2 | 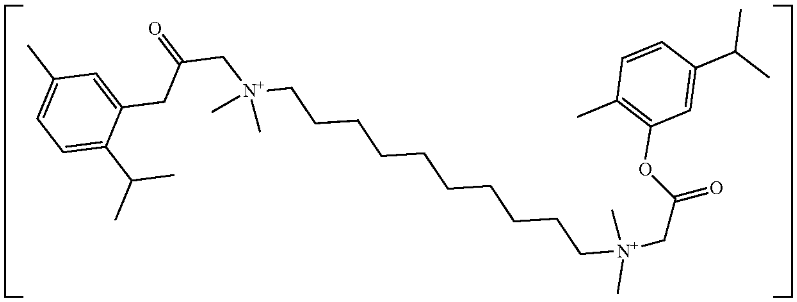 $2Cl^-$ |
| Formula V | 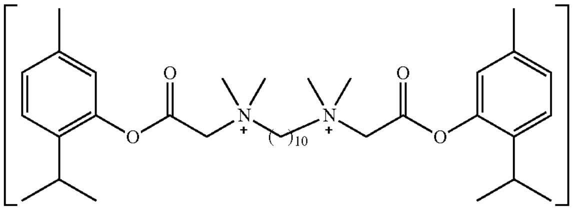 [$2Cl^-$] |
| Formula IV | 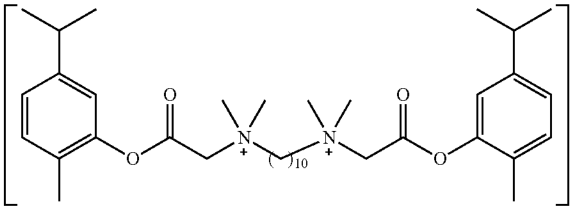 [$2Cl^-$] |
| Comparative compound 3 | 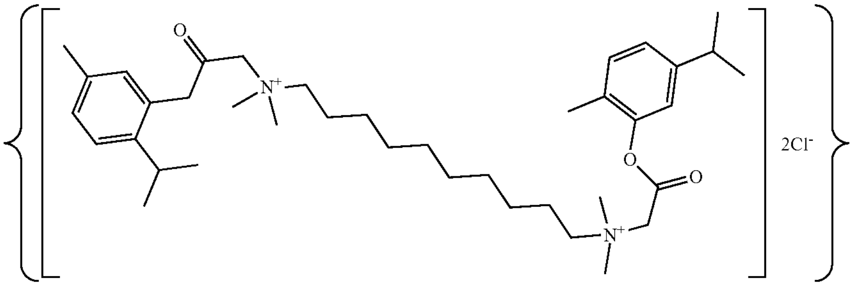 $2Cl^-$ $2Br_2$ |

TABLE 23-continued

| Compound | Structure |
|---|---|
| Formula XI | 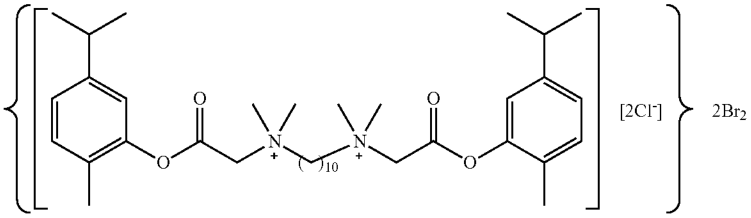 |

The invention claimed is:

1. A compound having the following formula:

(I)

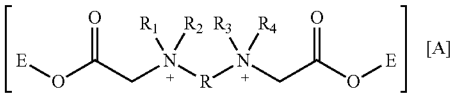

wherein R is an alkylene chain having between 8 and 20 carbon atoms, and A is one or more anions having a total charge of −2, or R is an amine having the following formula:

(Ia)

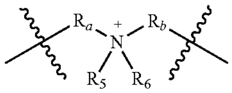

wherein $R_a$ and $R_b$ are each an alkylene chain having between 8 and 20 carbon atoms, and A is one or more anions having a total charge of −3;

$R_1$, $R_2$, $R_3$, $R_4$, $R_5$ and $R_6$ are each independently selected from $C_{1-10}$ alkyl and H;

E has the following formula (Ib)

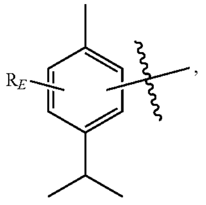

wherein the ester oxygen is bonded to the aromatic ring of each E at the same position, the position being position 2 or 3; and wherein RE is H or a halide.

2. A compound according to claim 1, having the following formula:

(II)

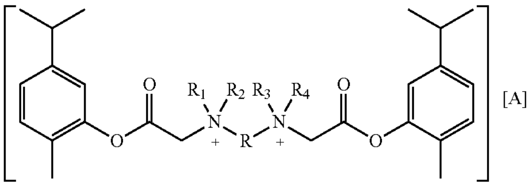 or (III)

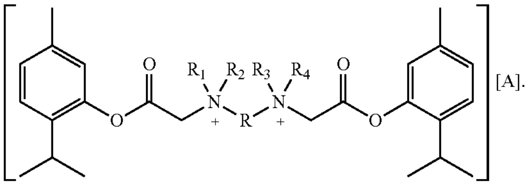

3. A compound according to claim 1, wherein $R_1$, $R_2$, $R_3$, $R_4$, $R_5$ and $R_6$ are each methyl.

4. A compound according to claim 1, having the following formulae:

(IV)

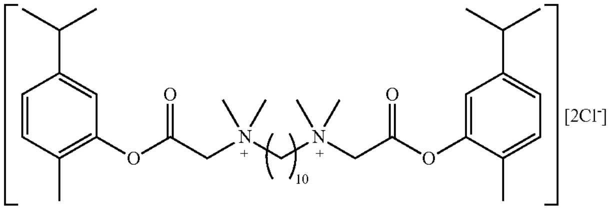 or

-continued (V)

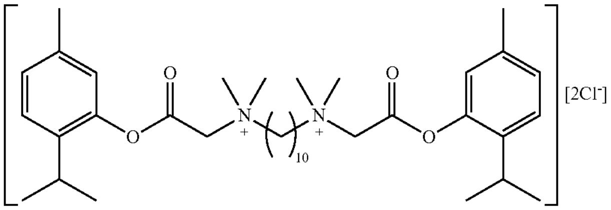

or (VI)

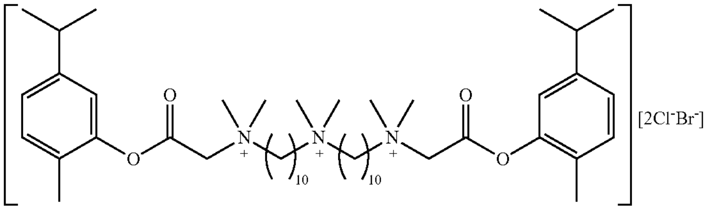

or (VII)

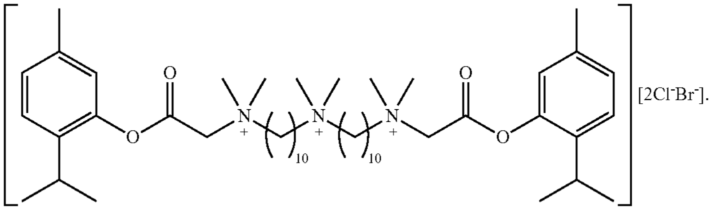

.

5. A compound having the following formula:

(VIII)

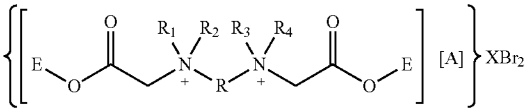

wherein R is an alkylene chain having between 8 and 20 carbon atoms, and A is one or more anions having a total charge of −2, or R is an amine having the following formula:

(Ia)

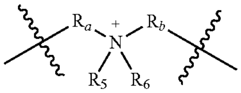

wherein $R_a$ and $R_b$ are each an alkylene chain having between 8 and 20 carbon atoms, and A is one or more anions having a total charge of −3;

$R_1$, $R_2$, $R_3$, $R_4$, $R_5$ and $R_6$ are each independently selected from $C_{1-10}$ alkyl and H;

E has the following formula (Ib)

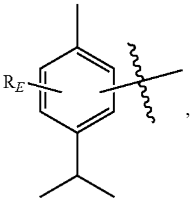

, wherein the ester oxygen is bonded to the aromatic ring of each E at the same position, the position being 2 or 3;

wherein RE is H or a halide and wherein X is 2, 3, 4 or 6.

6. A compound according to claim 5 having the following formula:

(IX)

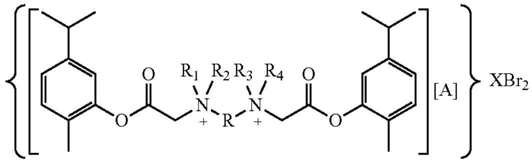

or (X)

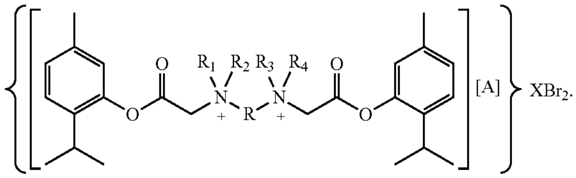

.

7. A compound according to claim 1, 2, 5 or 6, wherein R is a saturated linear alkylene chain having between 8 and 16 carbon atoms.

8. A compound according to claim 1, 2, 5 or 6, wherein $R_a$ and $R_b$ are each a saturated linear alkylene chain having between 8 and 16 carbon atoms.

9. A compound according to claim 1, 2, 5 or 6, wherein the one or more anions are selected from chloride anions and bromide anions.

10. A compound according to claim 5 or 6 having the following formula:

(XI)

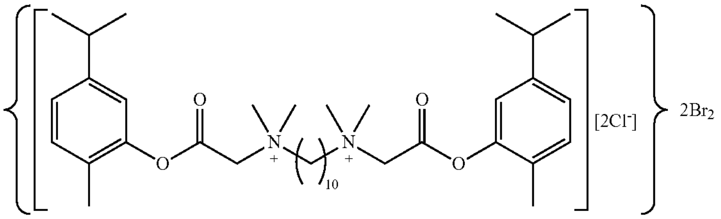

or (XII)

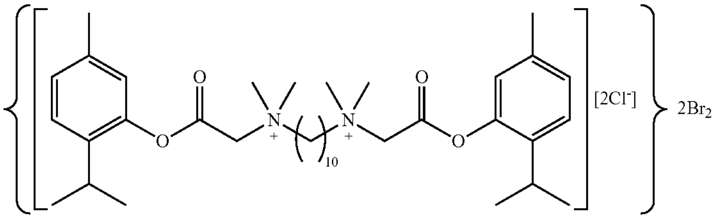

or (XIII)

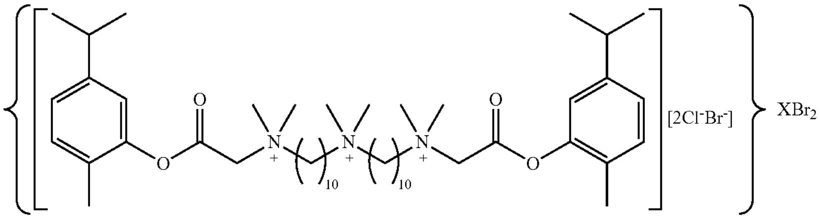

or (XIV)

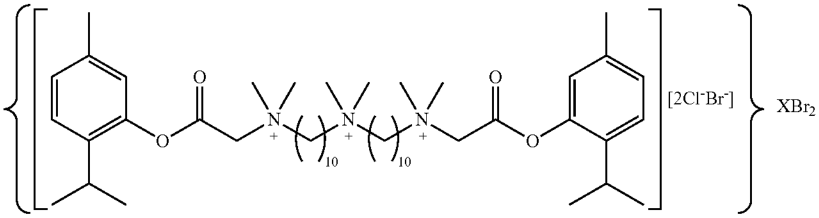

wherein X is 3 or 6.

11. A pharmaceutical composition comprising the compound of any of claim 1, 2, or 3-6.

12. A compound according to any one of claim 1, 2, or 3-6 for use as a medicament.

13. A compound according to any one of claim 1, 2, or 3-6 for use in the treatment of fungal infections and/or bacterial infections.

14. A compound according to any one of claim 1, 2, or 3-6 for use in the treatment of Herpes virus and/or Human Papilloma virus.

15. A process for producing the compound according to claim 1 comprising:

i) reacting a compound having the formula (XV)

(XV)

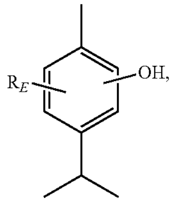

wherein the alcohol group is bonded to the benzene ring in position 2 or 3, and RE is H or a halide, with $R_7CH_2COCl$ to form a compound having the formula (XVI):

(XVI)

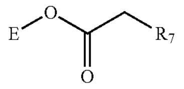

wherein $R_7$ is chlorine or bromine, E is (Ib)

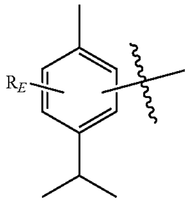

wherein the ester oxygen is bonded to the aromatic ring of E at position 2 or 3, and wherein RE is H or a halide; and ii) reacting 1 molar equivalents of the compound having the formula (XVII)

(XVII)

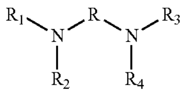

with 2 molar equivalent of the compound having formula (XVI) to form a compound having the formula (I)

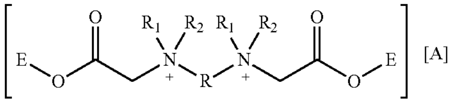

wherein R is an alkylene chain having between 8 and 20 carbon atoms, and A is one or more anions having a total charge of −2;

or R is an amine having the following formula:

(Ia)

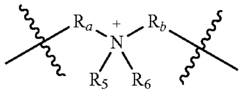

wherein $R_a$ and $R_b$ are each an alkylene chain having between 8 and 20 carbon atoms, and A is one or more anions having a total charge of −3;

E has the following formula (Ib)

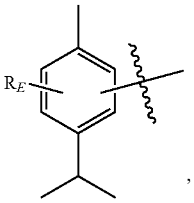

, wherein the ester oxygen is bonded to the aromatic ring of each E at the same position, the position being position 2 or 3 and wherein RE is H or a halide;

$R_1$, $R_2$, $R_3$, $R_4$, $R_5$ and $R_6$ are each independently selected from $C_{1-10}$ alkyl and H.

16. The process according to claim 15, wherein the reactions of step II is carried out in acetonitrile as solvent.

17. A process for the production of a compound according to claim 5 comprising reacting the compound having formula (I)

(I)

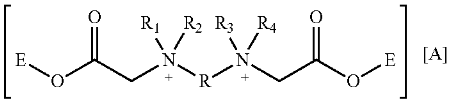

with bromine to form a compound having formula (VIII)

(VIII)

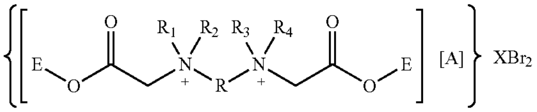

wherein R is an alkylene chain having between 8 and 20 carbon atoms, and A is one or more anions having a total charge of −2, or R is an amine having the following formula:

(Ia)

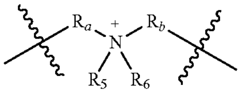

wherein $R_a$ and $R_b$ are each an alkylene chain having between 8 and 20 carbon atoms, and A is one or more anions having a total charge of −3;

$R_1$, $R_2$, $R_3$, $R_4$, $R_5$ and $R_6$ are each independently selected from $C_{1-10}$ alkyl and H;

E has the following formula (Ib)

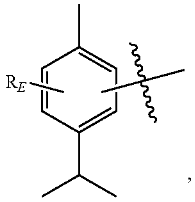

, wherein the ester oxygen is bonded to the aromatic ring of each E at the same position, the position being 2 or 3;

wherein RE is H or a halide; and wherein X is 2, 3, 4 or 6.

18. A compound according to claim 1, 2, 5 or 6, wherein R is a saturated linear alkylene chain having 10 carbon atoms.

19. A compound according to claim 1, 2, 5 or 6, wherein $R_a$ and $R_b$ are each a saturated linear alkylene chain having 10 carbon atoms.

* * * * *